(12) United States Patent
Hunter et al.

(10) Patent No.: US 8,548,565 B2
(45) Date of Patent: Oct. 1, 2013

(54) REGISTRATION OF HUMAN ANATOMY INTEGRATED FOR ELECTROMAGNETIC LOCALIZATION

(75) Inventors: Mark W. Hunter, Broomfield, CO (US); Paul Kessman, Lakewood, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 318 days.

(21) Appl. No.: 12/697,841

(22) Filed: Feb. 1, 2010

(65) Prior Publication Data
US 2010/0137707 A1    Jun. 3, 2010

Related U.S. Application Data

(63) Continuation of application No. 10/103,685, filed on Mar. 21, 2002, now Pat. No. 7,657,300, which is a continuation of application No. 09/429,569, filed on Oct. 28, 1999, now Pat. No. 6,381,485.

(51) Int. Cl.
*A61B 5/05*    (2006.01)
(52) U.S. Cl.
USPC ............................................ 600/424
(58) Field of Classification Search
USPC ................................. 600/424, 407
See application file for complete search history.

(56) References Cited

U.S. PATENT DOCUMENTS

| | | | |
|---|---|---|---|
| 1,576,781 A | 3/1926 | Phillips | |
| 1,735,726 A | 11/1929 | Bornhardt | |
| 2,407,845 A | 9/1946 | Nemeyer | |
| 2,650,588 A | 9/1953 | Drew | |
| 2,697,433 A | 12/1954 | Sehnder | |
| 3,016,899 A | 1/1962 | Stenvall | |

(Continued)

FOREIGN PATENT DOCUMENTS

| | | |
|---|---|---|
| CA | 964149 | 3/1975 |
| DE | 3042343 | 6/1982 |

(Continued)

OTHER PUBLICATIONS

"Prestige Cervical Disc System Surgical Technique", 12 pgs.

(Continued)

*Primary Examiner* — Jacqueline Cheng
(74) *Attorney, Agent, or Firm* — Harness, Dickey

(57) ABSTRACT

A method for use during a procedure on a body. The method generates a display representing relative positions of two structures during the procedure. The method comprises the steps of storing an image data set in memory, the image data set representing the position of the body based on scans taken of the body prior to the procedure; reading the image data set stored in the memory, the image data set having a plurality of data points in known relation to a plurality of reference points for at least one of the two structures; placing one or more magnetic field sensors in known relation to the reference points of the two structures; generating a magnetic field; detecting the magnetic field with the magnetic field sensors; ascertaining the locations of the sensors based upon the magnetic field detected by the sensors and processing the locations of the sensors to generate a displaced image data set representing the relative position of the two structures during the procedure; and generating a display based on the displaced image data set illustrating the relative position of the two structures during the procedure.

20 Claims, 5 Drawing Sheets

(56) References Cited

U.S. PATENT DOCUMENTS

| | | |
|---|---|---|
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |

| | | | | | |
|---|---|---|---|---|---|
| 5,079,699 A | 1/1992 | Tuy et al. | 5,330,485 A | 7/1994 | Clayman et al. |
| 5,086,401 A | 2/1992 | Glassman et al. | 5,333,168 A | 7/1994 | Fernandes et al. |
| 5,094,241 A | 3/1992 | Allen | 5,353,795 A | 10/1994 | Souza et al. |
| 5,097,839 A | 3/1992 | Allen | 5,353,800 A | 10/1994 | Pohndorf et al. |
| 5,098,426 A | 3/1992 | Sklar et al. | 5,353,807 A | 10/1994 | DeMarco |
| 5,099,845 A | 3/1992 | Besz et al. | 5,359,417 A | 10/1994 | Muller et al. |
| 5,099,846 A | 3/1992 | Hardy | 5,368,030 A | 11/1994 | Zinreich et al. |
| 5,105,829 A | 4/1992 | Fabian et al. | 5,371,778 A | 12/1994 | Yanof et al. |
| 5,107,839 A | 4/1992 | Houdek et al. | 5,375,596 A | 12/1994 | Twiss et al. |
| 5,107,843 A | 4/1992 | Aarnio et al. | 5,377,678 A | 1/1995 | Dumoulin et al. |
| 5,107,862 A | 4/1992 | Fabian et al. | 5,383,454 A | 1/1995 | Bucholz |
| 5,109,194 A | 4/1992 | Cantaloube | 5,385,146 A | 1/1995 | Goldreyer |
| 5,119,817 A | 6/1992 | Allen | 5,385,148 A | 1/1995 | Lesh et al. |
| 5,142,930 A | 9/1992 | Allen et al. | 5,386,828 A | 2/1995 | Owens et al. |
| 5,143,076 A | 9/1992 | Hardy et al. | 5,389,101 A | 2/1995 | Heilbrun et al. |
| 5,152,288 A | 10/1992 | Hoenig et al. | 5,391,199 A | 2/1995 | Ben-Haim |
| 5,160,337 A | 11/1992 | Cosman | 5,394,457 A | 2/1995 | Leibinger et al. |
| 5,161,536 A | 11/1992 | Vilkomerson et al. | 5,394,875 A | 3/1995 | Lewis et al. |
| 5,178,164 A | 1/1993 | Allen | 5,397,329 A | 3/1995 | Allen |
| 5,178,621 A | 1/1993 | Cook et al. | 5,398,684 A | 3/1995 | Hardy |
| 5,186,174 A | 2/1993 | Schlondorff et al. | 5,399,146 A | 3/1995 | Nowacki et al. |
| 5,187,475 A | 2/1993 | Wagener et al. | 5,400,384 A | 3/1995 | Fernandes et al. |
| 5,188,126 A | 2/1993 | Fabian et al. | 5,402,801 A | 4/1995 | Taylor |
| 5,190,059 A | 3/1993 | Fabian et al. | 5,408,409 A | 4/1995 | Glassman et al. |
| 5,193,106 A | 3/1993 | DeSena | 5,413,573 A | 5/1995 | Koivukangas |
| 5,197,476 A | 3/1993 | Nowacki et al. | 5,417,210 A | 5/1995 | Funda et al. |
| 5,197,965 A | 3/1993 | Cherry et al. | 5,419,325 A | 5/1995 | Dumoulin et al. |
| 5,198,768 A | 3/1993 | Keren | 5,423,334 A | 6/1995 | Jordan |
| 5,198,877 A | 3/1993 | Schulz | 5,425,367 A | 6/1995 | Shapiro et al. |
| 5,207,688 A | 5/1993 | Carol | 5,425,382 A | 6/1995 | Golden et al. |
| 5,211,164 A | 5/1993 | Allen | 5,426,683 A | 6/1995 | O'Farrell, Jr. et al. |
| 5,211,165 A | 5/1993 | Dumoulin et al. | 5,426,687 A | 6/1995 | Goodall et al. |
| 5,211,176 A | 5/1993 | Ishiguro et al. | 5,427,097 A | 6/1995 | Depp |
| 5,212,720 A | 5/1993 | Landi et al. | 5,429,132 A | 7/1995 | Guy et al. |
| 5,214,615 A | 5/1993 | Bauer | 5,433,198 A | 7/1995 | Desai |
| 5,219,351 A | 6/1993 | Teubner et al. | RE35,025 E | 8/1995 | Anderton |
| 5,222,499 A | 6/1993 | Allen et al. | 5,437,277 A | 8/1995 | Dumoulin et al. |
| 5,224,049 A | 6/1993 | Mushabac | 5,443,066 A | 8/1995 | Dumoulin et al. |
| 5,228,442 A | 7/1993 | Imran | 5,443,489 A | 8/1995 | Ben-Haim |
| 5,230,338 A | 7/1993 | Allen et al. | 5,444,756 A | 8/1995 | Pai et al. |
| 5,230,623 A | 7/1993 | Guthrie et al. | 5,445,144 A | 8/1995 | Wodicka et al. |
| 5,233,990 A | 8/1993 | Barnea | 5,445,150 A | 8/1995 | Dumoulin et al. |
| 5,237,996 A | 8/1993 | Waldman et al. | 5,445,166 A | 8/1995 | Taylor |
| 5,249,581 A | 10/1993 | Horbal et al. | 5,446,548 A | 8/1995 | Gerig et al. |
| 5,251,127 A | 10/1993 | Raab | 5,447,154 A | 9/1995 | Cinquin et al. |
| 5,251,635 A | 10/1993 | Dumoulin et al. | 5,448,610 A | 9/1995 | Yamamoto et al. |
| 5,253,647 A | 10/1993 | Takahashi et al. | 5,453,686 A | 9/1995 | Anderson |
| 5,255,680 A | 10/1993 | Darrow et al. | 5,456,718 A | 10/1995 | Szymaitis |
| 5,257,636 A | 11/1993 | White | 5,457,641 A | 10/1995 | Zimmer et al. |
| 5,257,998 A | 11/1993 | Ota et al. | 5,458,718 A | 10/1995 | Venkitachalam |
| 5,261,404 A | 11/1993 | Mick et al. | 5,464,446 A | 11/1995 | Dreessen et al. |
| 5,265,610 A | 11/1993 | Darrow et al. | 5,469,847 A | 11/1995 | Zinreich et al. |
| 5,265,611 A | 11/1993 | Hoenig et al. | 5,478,341 A | 12/1995 | Cook et al. |
| 5,269,759 A | 12/1993 | Hernandez et al. | 5,478,343 A | 12/1995 | Ritter |
| 5,271,400 A | 12/1993 | Dumoulin et al. | 5,480,422 A | 1/1996 | Ben-Haim |
| 5,273,025 A | 12/1993 | Sakiyama et al. | 5,480,439 A | 1/1996 | Bisek et al. |
| 5,274,551 A | 12/1993 | Corby, Jr. | 5,483,961 A | 1/1996 | Kelly et al. |
| 5,279,309 A | 1/1994 | Taylor et al. | 5,485,849 A | 1/1996 | Panescu et al. |
| 5,285,787 A | 2/1994 | Machida | 5,487,391 A | 1/1996 | Panescu |
| 5,291,199 A | 3/1994 | Overman et al. | 5,487,729 A | 1/1996 | Avellanet et al. |
| 5,291,889 A | 3/1994 | Kenet et al. | 5,487,757 A | 1/1996 | Truckai et al. |
| 5,295,483 A | 3/1994 | Nowacki et al. | 5,490,196 A | 2/1996 | Rudich et al. |
| 5,297,549 A | 3/1994 | Beatty et al. | 5,494,034 A | 2/1996 | Schlondorff et al. |
| 5,299,253 A | 3/1994 | Wessels | 5,503,416 A | 4/1996 | Aoki et al. |
| 5,299,254 A | 3/1994 | Dancer et al. | 5,513,637 A | 5/1996 | Twiss et al. |
| 5,299,288 A | 3/1994 | Glassman et al. | 5,514,146 A | 5/1996 | Lam et al. |
| 5,300,080 A | 4/1994 | Clayman et al. | 5,515,160 A | 5/1996 | Schulz et al. |
| 5,305,091 A | 4/1994 | Gelbart et al. | 5,517,990 A | 5/1996 | Kalfas et al. |
| 5,305,203 A | 4/1994 | Raab | 5,531,227 A | 7/1996 | Schneider |
| 5,306,271 A | 4/1994 | Zinreich et al. | 5,531,520 A | 7/1996 | Grimson et al. |
| 5,307,072 A | 4/1994 | Jones, Jr. | 5,542,938 A | 8/1996 | Avellanet et al. |
| 5,309,913 A | 5/1994 | Kormos et al. | 5,543,951 A | 8/1996 | Moehrmann |
| 5,315,630 A | 5/1994 | Sturm et al. | 5,546,940 A | 8/1996 | Panescu et al. |
| 5,316,024 A | 5/1994 | Hirschi et al. | 5,546,949 A | 8/1996 | Frazin et al. |
| 5,318,025 A | 6/1994 | Dumoulin et al. | 5,546,951 A | 8/1996 | Ben-Haim |
| 5,320,111 A | 6/1994 | Livingston | 5,551,429 A | 9/1996 | Fitzpatrick et al. |
| 5,325,728 A | 7/1994 | Zimmerman et al. | 5,558,091 A * | 9/1996 | Acker et al. .................. 600/424 |
| 5,325,873 A | 7/1994 | Hirschi et al. | 5,566,681 A | 10/1996 | Manwaring et al. |
| 5,329,944 A | 7/1994 | Fabian et al. | 5,568,384 A | 10/1996 | Robb et al. |

| Patent | Date | Inventor |
|---|---|---|
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,255 A | 6/1997 | Ellis et al. |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,697,377 A | 12/1997 | Wittkampf |
| 5,702,406 A | 12/1997 | Vilsmeier et al. |
| 5,706,811 A | 1/1998 | Takeda et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A * | 9/1998 | Ferre et al. .................. 128/897 |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,957,844 A | 9/1999 | Dekel et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |

| | | | | | | |
|---|---|---|---|---|---|---|
| 6,063,022 | A | 5/2000 | Ben-Haim | 2006/0036189 A1 | 2/2006 | Martinelli et al. |
| 6,071,288 | A | 6/2000 | Carol et al. | 2010/0210939 A1 | 8/2010 | Hartmann et al. |
| 6,073,043 | A | 6/2000 | Schneider | 2010/0331671 A1 | 12/2010 | Martinelli et al. |
| 6,076,008 | A | 6/2000 | Bucholz | | | |
| 6,096,050 | A | 8/2000 | Audette | | | |

FOREIGN PATENT DOCUMENTS

| | | | |
|---|---|---|---|
| 6,104,944 | A | 8/2000 | Martinelli |
| 6,118,845 | A | 9/2000 | Simon et al. |
| 6,122,538 | A | 9/2000 | Sliwa, Jr. et al. |
| 6,122,541 | A | 9/2000 | Cosman et al. |
| 6,131,396 | A | 10/2000 | Duerr et al. |
| 6,139,183 | A | 10/2000 | Graumann |
| 6,147,480 | A | 11/2000 | Osadchy et al. |
| 6,149,592 | A | 11/2000 | Yanof et al. |
| 6,156,067 | A | 12/2000 | Bryan et al. |
| 6,161,032 | A | 12/2000 | Acker |
| 6,165,181 | A | 12/2000 | Heilbrun et al. |
| 6,167,296 | A | 12/2000 | Shahidi |
| 6,172,499 | B1 | 1/2001 | Ashe |
| 6,175,756 | B1 | 1/2001 | Ferre et al. |
| 6,178,345 | B1 | 1/2001 | Vilsmeier et al. |
| 6,194,639 | B1 | 2/2001 | Botella et al. |
| 6,201,387 | B1 | 3/2001 | Govari |
| 6,203,497 | B1 | 3/2001 | Dekel et al. |
| 6,211,666 | B1 | 4/2001 | Acker |
| 6,223,067 | B1 | 4/2001 | Vilsmeier et al. |
| 6,233,476 | B1 | 5/2001 | Strommer et al. |
| 6,235,038 | B1 | 5/2001 | Hunter et al. |
| 6,246,231 | B1 | 6/2001 | Ashe |
| 6,259,942 | B1 | 7/2001 | Westermann et al. |
| 6,259,943 | B1 | 7/2001 | Cosman et al. |
| 6,273,896 | B1 | 8/2001 | Franck et al. |
| 6,282,437 | B1 * | 8/2001 | Franck et al. .................. 600/429 |
| 6,285,902 | B1 | 9/2001 | Kienzle, III et al. |
| 6,298,262 | B1 | 10/2001 | Franck et al. |
| 6,314,310 | B1 * | 11/2001 | Ben-Haim et al. ............ 600/424 |
| 6,332,089 | B1 | 12/2001 | Acker et al. |
| 6,333,971 | B2 | 12/2001 | McCrory et al. |
| 6,341,231 | B1 | 1/2002 | Ferre et al. |
| 6,351,659 | B1 | 2/2002 | Vilsmeier |
| 6,379,302 | B1 | 4/2002 | Kessman et al. |
| 6,381,485 | B1 | 4/2002 | Hunter et al. |
| 6,402,762 | B2 | 6/2002 | Hunter et al. |
| 6,405,072 | B1 | 6/2002 | Cosman |
| 6,424,856 | B1 | 7/2002 | Vilsmeier et al. |
| 6,427,314 | B1 | 8/2002 | Acker |
| 6,428,547 | B1 | 8/2002 | Vilsmeier et al. |
| 6,434,415 | B1 | 8/2002 | Foley et al. |
| 6,437,567 | B1 | 8/2002 | Schenck et al. |
| 6,445,943 | B1 | 9/2002 | Ferre et al. |
| 6,470,207 | B1 | 10/2002 | Simon et al. |
| 6,474,341 | B1 | 11/2002 | Hunter et al. |
| 6,478,802 | B2 | 11/2002 | Kienzle, III et al. |
| 6,484,049 | B1 | 11/2002 | Seeley et al. |
| 6,490,475 | B1 | 12/2002 | Seeley et al. |
| 6,493,573 | B1 | 12/2002 | Martinelli et al. |
| 6,498,944 | B1 | 12/2002 | Ben-Haim et al. |
| 6,499,488 | B1 | 12/2002 | Hunter et al. |
| 6,516,046 | B1 | 2/2003 | Frohlich et al. |
| 6,527,443 | B1 | 3/2003 | Vilsmeier et al. |
| 6,551,325 | B2 | 4/2003 | Neubauer et al. |
| 6,584,174 | B2 | 6/2003 | Schubert et al. |
| 6,609,022 | B2 | 8/2003 | Vilsmeier et al. |
| 6,611,700 | B1 | 8/2003 | Vilsmeier et al. |
| 6,640,128 | B2 | 10/2003 | Vilsmeier et al. |
| 6,669,635 | B2 | 12/2003 | Kessman et al. |
| 6,675,040 | B1 | 1/2004 | Cosman |
| 6,694,162 | B2 | 2/2004 | Hartlep |
| 6,701,179 | B1 | 3/2004 | Martinelli et al. |
| 6,747,539 | B1 | 6/2004 | Martinelli |
| 6,968,224 | B2 | 11/2005 | Kessman et al. |
| 7,007,699 | B2 | 3/2006 | Martinelli et al. |
| 7,152,608 | B2 | 12/2006 | Hunter et al. |
| 7,657,300 | B2 | 2/2010 | Hunter et al. |
| 7,797,032 | B2 | 9/2010 | Martinelli et al. |
| 2001/0007918 | A1 | 7/2001 | Vilsmeier et al. |
| 2002/0095081 | A1 | 7/2002 | Vilsmeier et al. |
| 2004/0024309 | A1 | 2/2004 | Ferre et al. |

| | | |
|---|---|---|
| DE | 3508730 | 9/1986 |
| DE | 3717871 | 12/1988 |
| DE | 3831278 A1 | 3/1989 |
| DE | 3838011 | 7/1989 |
| DE | 4213426 A1 | 10/1992 |
| DE | 4225112 | 12/1993 |
| DE | 4233978 | 4/1994 |
| DE | 19715202 | 10/1998 |
| DE | 19751761 | 10/1998 |
| DE | 19832296 | 2/1999 |
| DE | 19747427 | 5/1999 |
| DE | 10085137 | 11/2002 |
| EP | 0062941 | 10/1982 |
| EP | 0119660 | 9/1984 |
| EP | 0155857 | 9/1985 |
| EP | 0319844 | 6/1989 |
| EP | 0326768 | 8/1989 |
| EP | 350996 A1 | 1/1990 |
| EP | 0359773 A1 | 3/1990 |
| EP | 0419729 A1 | 4/1991 |
| EP | 0427358 | 5/1991 |
| EP | 0456103 | 11/1991 |
| EP | 0469966 A1 | 2/1992 |
| EP | 0501993 A1 | 9/1992 |
| EP | 0581704 | 2/1994 |
| EP | 0651968 | 5/1995 |
| EP | 0655138 | 5/1995 |
| EP | 0894473 A2 | 2/1999 |
| EP | 0908146 | 4/1999 |
| EP | 0930046 | 7/1999 |
| FR | 2417970 | 9/1979 |
| FR | 2618211 A1 | 1/1989 |
| GB | 2094590 A | 9/1982 |
| GB | 2164856 A | 4/1986 |
| JP | 62327 | 1/1983 |
| JP | 2765738 | 6/1988 |
| JP | 63240851 | 10/1988 |
| JP | 3267054 | 11/1991 |
| JP | 6194639 | 7/1994 |
| WO | WO-8809151 | 12/1988 |
| WO | WO-8905123 | 6/1989 |
| WO | WO-9005494 A1 | 5/1990 |
| WO | WO-9103982 A1 | 4/1991 |
| WO | WO-9104711 | 4/1991 |
| WO | WO-9107726 | 5/1991 |
| WO | WO-9203090 | 3/1992 |
| WO | WO-9206645 | 4/1992 |
| WO | WO-9404938 | 3/1994 |
| WO | WO-9423647 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |
| WO | WO-9838908 | 9/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |
| WO | WO-9952094 A1 | 10/1999 |
| WO | WO-9960939 A1 | 12/1999 |
| WO | WO-0130437 A1 | 5/2001 |

OTHER PUBLICATIONS

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel, E. et al., Magnetic Source Imaging: A Review of the Magnes System of Biomagnetic Technologies Incorporated, Neurosurgery, vol. 33, No. 2 (Aug. 1993).

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

BrainLab marketing brochures for Vector Vision (undated) (26 pages).

Brown, R., M.D., A Stereotactic Head Frame for Use with CT Body Scanners, Investigative Radiology .Copyrgt. J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).

Bucholz, R.D., et al., Variables affecting the accuracy of stereotactic localization using computerized tomography, J. Neurosurg., vol. 79, pp. 667-673 (1993).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," International Advanced Robotics Programme, Sep. 1989, pp. 63-65.

Cinquin, P. et al., Computer Assisted Medical Interventions, IEEE, pp. 254-263 (May/Jun. 1995).

Clarysse, P. et al., A Computer-Assisged System for 3-D Frameless Localization in Stereotaxic MRI, IEEE Trans. on Med. Imaging, vol. 10, No. 4, pp. 523-529 (Dec. 1991).

Cutting M.D. et al., Optical Tracking of Bone Fragments During Craniofacial Surgery, Second Annual International Symposium on Medical Robotics and Computer Assisted Surgery, pp. 221-225, (Nov. 1995).

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley, K.T., et al., Image-guided Intraoperative Spinal Localization, Intraoperative Neuroprotection, Chapter 19, pp. 325-340 (1996).

Foley, K.T., et al., The StealthStation: Three-Dimensional Image-Interactive Guidance for the Spine Surgeon, Spinal Frontiers, pp. 7-9 (Apr. 1996).

Friets, E.M., et al. A Frameless Stereotaxic Operating Microscope for Neurosurgery, IEEE Trans. On Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164, (May 1, 1994) pp. 137-145.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image processing, Second Edition, 1987, pp. 52-54.

Gottesfeld Brown et al., "Registration of Planar Film Radiographs with Computer Tomography," Proceedings of MMBIA, Jun. '96, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: the Operating Arm System, Handbook of Stereotaxy Using the CRW Apparatus, Chapter 13, (1994) pp. 193-211.

Hamadeh et al, "Kinematic Study of Lumbar Spine Using Functional Radiographies and 3D/2D Registration," TIMC UMR 5525—IMAG (1997).

Hamadeh et al., "Automated 3-Dimensional Computed Tomographic and Fluoroscopic Image Registration," Computer Aided Surgery (1998), 3:11-19.

Hamadeh, A., et al., Toward automatic registration between CT and X-ray images: cooperation between 3D/2D registration and 2D edge detection, TIMC-IMAG, Faculte de Medecine de Grenoble, France, pp. 39-46 (1995) (Second Annual Intl. Symposium onMedical Robotics and Computer-Assisged Surgery, MRCAS '95, Nov. 4-7, 1995).

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, J.F., Reference-Display System for the Integration of CT Scanning and the Operating Microscope, IEEE, vol. 8, pp. 252-254, Proceedings of the Eleventh Annual Northeast Bioengineering Conference (Worcester, Massachusetts) (Mar. 14-15, 1985).

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Preliminary Experience with Brown-Roberts-Wells (BRW) computerized tomography stereotaxic guidance system, J. Neurosurg., vol. 59, pp. 217-222 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson, J.M., et al., an Accurate and Ergonomic Method of Registration for Image-guided Neurosurgery, Computerized Medical Imaging and Graphics, vol. 18, No. 4, pp. 273-277 (1994).

Hoerenz, "The Operating Microscope I. Optical Principles, Illumination Systems, and Support Systems," Journal of Microsurgery, vol. 1, 1980, pp. 364-369.

Hofstetter, R., et al., Fluroscopy Based Surgical Navigation-Concept and Clinical Applications, Computer Assisged Radiology and Surgery, Car '97, Proceed. of the 11th Intl. Symp. and Exh., Berlin, pp. 956-960 (Jun. 25-28, 1997).

Horner, N.B. et al., A Comparison of CT-Stereotaxic Brain Biopsy Techniques, Investig. Radiol., vol. 19, pp. 367-373 (Sep.-Oct. 1984).

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small Cns Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," Car '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intraaxial brain neoplasms," Journal of Neurosurgery, vol. 64, Mar. 1986, pp. 427-439.

Kelly et al., "Precision Resection of Intra-Axial CNA Lesions by CT-Based Stereotactic Craniotomy and Computer Monitored CO2 Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 717 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, (1996) pp. 635-638.

Kosugi, Y., et al., An Articulated Neurosurgical Navigation System Using MRI and CT Images, IEEE Trans. on Biomed, Eng. vol. 35, No. 2, pp. 147-152 (Feb. 1988).

Kosugi, Y., et al., An Articulated Neurosurgical Navigation System Using MRI and CT Images, IEEE Trans. on Biomed., Eng., vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Matching of Medical Images for Computed and Robot Assisted Surgery," IEEE EMBS, Orlando, 1991.

Lavallee, "VI Adaption de la Methodologie a Quelques Applications Cliniques," Chapitre VI, pp. 133-148.

Lavallee, S., et al., A new system for computer assisted neurosurgery, IEEE EMBS, 11th Annual Intl. Conf., pp. 926-927 (1989).

Lavallee, S., et al., Computer Assisted Interventionist Imaging: the Instance of Stereotactic Brain Surgery, MEDINFO 89, pp. 613-617 (1989).

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO Asi Series, vol. F 60, 3d Imaging in Medic., pp. 301-312 (1990).

Lavallee, S., et al., Computer Assisted Spine Surgery: a technique for accurate transpedicular screw fixation using CT data and a 3-D optical localizer, TIMC, Faculte de Medecine de Grenoble, J. of Image Guided Surg., vol. 1, No. 1, pp. 65-73 (1995).

Lavallee, S., et al., Image guided operating robot: a clinical application in stereotactic neurosurgery, IEEE Rob. And Autom. Society, Proc. of the 1992 Intl. Conf. on Rob. And Autom., May 1992, pp. 618-624, First Intl. Symp. on Med. Rob. and Comp.Assisted Surg. (Pittsburg, PA) (Sep. 22-24, 1994).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux, L., et al., A patient-to-computed-tomography image registration method based on digitally reconstructed radiographs, Med. Phys., vol. 21, No. 11, pp. 1749-1760 (1994).

Levin et al., "The Brain: Integrated Three-dimensional Display of MR and PET Images," Radiology, vol. 172, No. 3, Sep. 1989, pp. 783-789 1.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

Mazier, B., et al., Computer assisted interventionist imaging: application to the vertebral column surgery, Annual Intl. Conf. of the IEEE in Medic. and Biol. Soc., vol. 12, No. 1, pp. 430-431 (1990).

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, P., et al., Computer assisted Spine Surgery, Clinical Orthop. and Related Research, No. 337, pp. 86-96 (1997).

Ng, W.S. et al., Robotic Surgery—A First-Hand Experience in Transurethral Resection of the Prostate Surgery, IEEE Eng. in Med. and Biology, pp. 120-125 (Mar. 1993).

Pelizzari , C.A., et al., Accurate Three-Dimensional Registration of CT, PET, and/or MR Images of the Brain, Journal of Computer Assisted Tomography, vol. 13, No. 1, pp. 20-26 (Jan./Feb. 1989).

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, Hans. F., Neuronavigation: A Ten-Year Review, Neurosurgery, (1996) pp. 329-341.

Roberts, D.W., et al., A frameless stereotaxic integration of computerized tomographic imaging and the operating microscope. J. Neurosurg., vol. 65, pp. 545-549 (Oct. 1986).

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS (1995), pp. 185-192.

Smith et al., "Computer Methods for Improved Diagnostic Image Display Applied to Stereotactic Neurosurgery," Automedical, vol. 14, 1992, pp. 371-382 (4 unnumbered pages).

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Smith, K.R., et al., The Neurostation-a highly, accurate, minimally invasive solution to frameless stereotatic neurosurgery, Comput. Med. Imag. and Graph., vol. 18, No. 4, pp. 247256 (1994).

Stereotactic One, Affordable PC Based Graphics for Stereotactic Surgery, Stereotactic Image Systems, Inc. (SLC, Utah) (marketing brochure, undated).

Tan, K., Ph.D., et al., A frameless stereotactic approach to neurosurgical planning based on retrospective patient-image registration, J Neurosurgy, vol. 79, pp. 296-303 (Aug. 1993).

The Laitinen Stereoadapter 500, Instructions for use. By Surgical Navigation Technologies, FDA-NS-001A Rev. 0 (undated).

The Laitinen Stereotactic System, E2-E6.

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volumn Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," (1997) pp. 119-128.

* cited by examiner

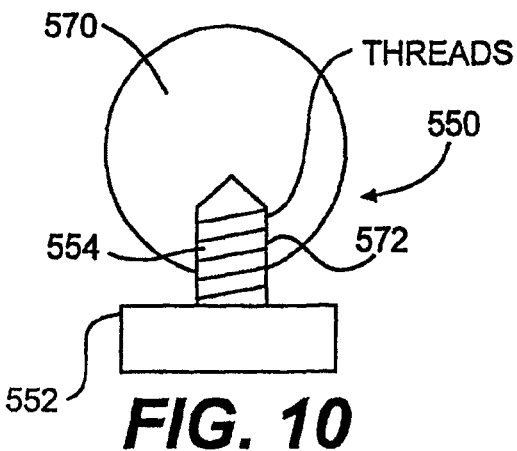
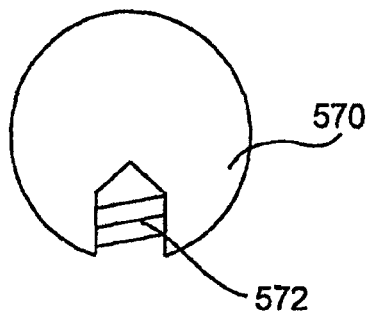
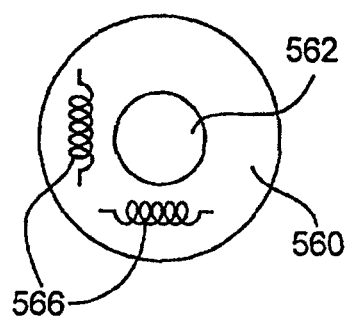
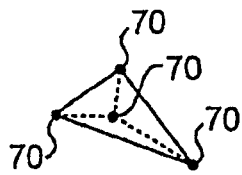
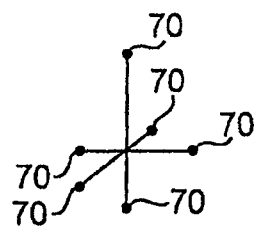
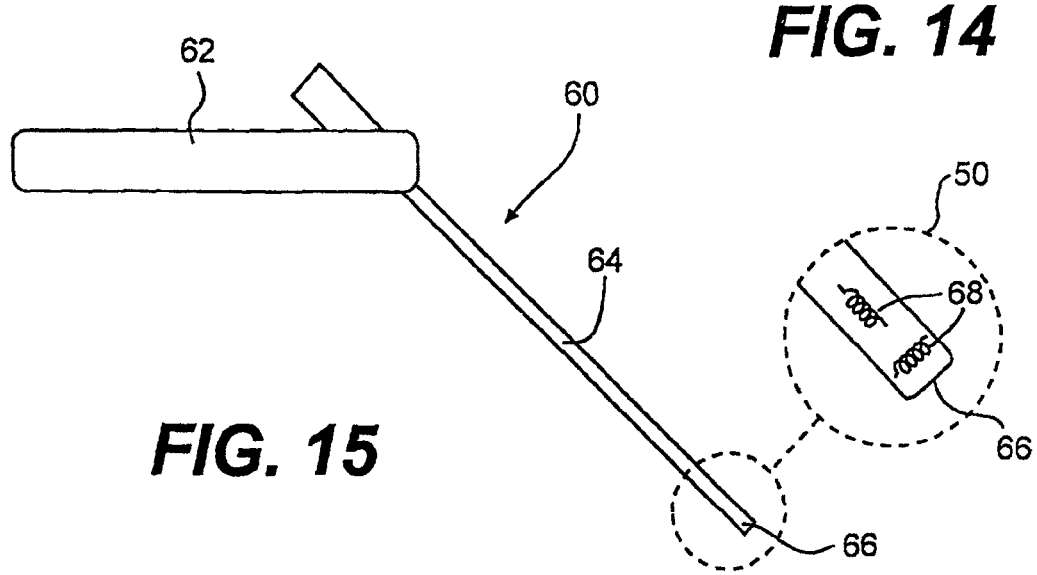

REGISTRATION OF HUMAN ANATOMY INTEGRATED FOR ELECTROMAGNETIC LOCALIZATION

CROSS-REFERENCE TO RELATED APPLICATIONS

This application is a continuation of U.S. patent application Ser. No. 10/103,685, filed Mar. 21, 2002, now U.S. Pat. No. 7,657,300, issued on Feb. 2, 2010, which is a continuation of U.S. Pat. No. 6,381,485, issued on Apr. 30, 2002, the applications which are hereby incorporated by reference herein.

The following United States patent applications, which were concurrently filed with this one on Oct. 28, 1999, are fully incorporated herein by reference: Method and System for Navigating a Catheter Probe in the Presence of Field-influencing Objects, by Michael Martinelli, Paul Kessman and Brad Jascob; Patient-shielding and Coil System, by Michael Martinelli, Paul Kessman and Brad Jascob; Navigation Information Overlay onto Ultrasound Imagery, by Paul Kessman, Troy Holsing and Jason Trobaugh; Coil Structures and Methods for Generating Magnetic Fields, by Brad Jascob, Paul Kessman and Michael Martinelli; Registration of Human Anatomy Integrated for Electromagnetic Localization, by Mark W. Hunter and Paul Kessman; System for Translation of Electromagnetic and Optical Localization Systems, by Mark W. Hunter and Paul Kessman; Surgical Communication and Power System, by Mark W. Hunter, Paul Kessman and Brad Jascob; and Surgical Sensor, by Mark W. Hunter, Sheri McCoid and Paul Kessman.

BACKGROUND OF THE INVENTION

The present invention relates to localization of a position during neurosurgery. The present invention relates more specifically to electromagnetic localization of a position during stereotactic neurosurgery, such as brain surgery and spinal surgery.

Precise localization of a position is important to stereotactic neurosurgery. In addition, minimizing invasiveness of surgery is important to reduce health risks for a patient. Stereotactic surgery minimizes invasiveness of surgical procedures by allowing a device to be guided through tissue that has been localized by preoperative scanning techniques, such as for example, MR, CT, ultrasound, fluoro and PET. Recent developments in stereotactic surgery have increased localization precision and helped minimize invasiveness of surgery.

Stereotactic neurosurgery is now commonly used in neurosurgery of the brain. Such methods typically involve acquiring image data by placing fiducial markers on the patient's head, scanning the patient's head, attaching a headring to the patient's head, and determining the spacial relation of the image data to the headring by, for example, registration of the fiducial markers. Registration of the fiducial markers relates the information in the scanned image data for the patient's brain to the brain itself, and involves one-to-one mapping between the fiducial markers as identified in the image data and the fiducial markers that remain on the patient's head after scanning and throughout surgery. This is referred to as registering image space to patient space. Often, the image space must also be registered to another image space. Registration is accomplished through knowledge of the coordinate vectors of at least three non-collinear points in the image space and the patient space.

Currently, registration for image guided surgery can be completed by different methods. First, point-to-point registration is accomplished by identifying points in image space and then touching the same points in patient space. Second, surface registration involves the user's generation of a surface (e.g., the patient's forehead) in patient space by either selecting multiple points or scanning, and then accepting or rejecting the best fit to that surface in image space, as chosen by the processor. Third, repeat fixation devices entail the user repeatedly removing and replacing a device in known relation to the fiducial markers. Such registration methods have additional steps during the procedure, and therefore increase the complexity of the system and increase opportunities for introduction of human error.

It is known to adhere the fiducial markers to a patient's skin or alternatively to implant the fiducial markers into a patient's bone for use during stereotactic surgery. For example, U.S. Pat. No. 5,595,193 discloses an apparatus and method for creating a hole that does not penetrate the entire thickness of a segment of bone and is sized to accommodate a fiducial marker. A fiducial marker may then be inserted into the hole and image data may be acquired.

Through the image data, quantitative coordinates of targets within the patient's body can be specified relative to the fiducial markers. Once a guide probe or other instrument has been registered to the fiducial markers on the patient's body, the instrument can be navigated through the patient's body using image data.

It is also known to display large, three-dimensional data sets of image data in an operating room or in the direct field of view of a surgical microscope. Accordingly, a graphical representation of instrument navigation through the patient's body is displayed on a computer screen based on reconstructed images of scanned image data.

Although scanners provide valuable information for stereotactic surgery, improved accuracy in defining the position of the target with respect to an accessible reference location can be desirable. Inaccuracies in defining the target position can create inaccuracies in placing a therapeutic probe. One method for attempting to limit inaccuracies in defining the target position involves fixing the patient's head to the scanner to preserve the reference. Such a requirement is uncomfortable for the patient and creates other inconveniences, particularly if surgical procedures are involved. Consequently, a need exists for a system utilizing a scanner to accurately locate positions of targets, which allows the patient to be removed from the scanner.

Stereotactic neurosurgery utilizing a three-dimensional digitizer allows a patient to be removed from the scanner while still maintaining accuracy for locating the position of targets. The three-dimensional digitizer is used as a localizer to determine the intra-procedural relative positions of the target. Three-dimensional digitizers may employ optical, acoustic, electromagnetic, conductive or other known three-dimensional navigation technology for navigation through the patient space.

Stereotactic surgery techniques are also utilized for spinal surgery in order to increase accuracy of the surgery and minimize invasiveness. Accuracy is particularly difficult in spinal surgery and must be accommodated in registration and localization techniques utilized in the surgery. Prior to spinal surgery, the vertebra are scanned to determine their alignment and positioning. During imaging, scans are taken at intervals through the vertebra to create a three-dimensional pre-procedural data set for the vertebra. After scanning the patient is moved to the operating table, which can cause repositioning of the vertebra. In addition, the respective positions of the vertebra may shift once the patient has been immobilized on the operating table because, unlike the brain, the spine is not held relatively still in the same way as a skull-like enveloping structure. Even normal patient respiration may cause relative movement of the vertebra.

Computer processes discriminate the image data retrieved by scanning the spine so that the body vertebra remain in memory. Once the vertebra are each defined as a single rigid body, the vertebra can be repositioned with software algorithms that define a displaced image data set. Each rigid body element has at least three fiducial markers that are visible on the pre-procedural images and accurately detectable during the procedure. It is preferable to select reference points on the spinous process that are routinely exposed during such surgery. See also, for example, U.S. Pat. No. 5,871,445, WO 96/11624, U.S. Pat. Nos. 5,592,939 and 5,697,377, the disclosures of which are incorporated herein by reference.

SUMMARY OF INVENTION

To enhance the prior art, and in accordance with the purposes of the invention, as embodied and broadly described herein, there is provided a system for displaying relative positions of two structures during a procedure on a body. The system comprises memory for storing an image data set representing the position of the body based on scans of the body, the image data set having a plurality of data points in known relation to a plurality of reference points for the body; a magnetic field generator for generating a magnetic field to be sensed by one or more magnetic field sensors placed in known relation to the reference points of the body for detecting the magnetic field and for generating positional signals in response to the detected magnetic field; a processor for receiving the reference signals and for ascertaining a location of the magnetic field sensors based upon the reference signals, the processor for generating a displaced image data set representing the relative positions of the body elements during the procedure; and a display utilizing the displaced image data set generated by the processor to display the relative position of the body elements during the procedure.

The present invention also provides a method for use during a procedure on a body. The method generates a display representing relative positions of two structures during the procedure. The method comprises the steps of storing an image data set in memory, the image data set representing the position of the body based on scans taken of the body prior to the procedure; reading the image data set stored in the memory, the image data set having a plurality of data points in known relation to a plurality of reference points for at least one of the two structures; placing one or more magnetic field sensors in known relation to the reference points of the two structures; generating a magnetic field; detecting the magnetic field with the magnetic field sensors; ascertaining the locations of the sensors based upon the magnetic field detected by the sensors and processing the locations of the sensors to generate a displaced image data set representing the relative position of the two structures during the procedure; and generating a display based on the displaced image data set illustrating the relative position of the two structures during the procedure.

The present invention further includes a device for use in a system for displaying relative positions of two structures during a procedure on a body. The device comprises a base adapted for attachment to the body, a fiducial marker mounted to the base, and a sensor having a known location and orientation with respect to the fiducial marker.

Additional features and advantages of the invention will be set forth in the description which follows, and in part will be apparent from the description, or may be learned from practice of the invention. The objectives and other advantages of the invention will be realized and attained by the apparatus particularly pointed out in the written description and claims herein as well as the appended drawings.

BRIEF DESCRIPTION OF THE DRAWINGS

The accompanying drawings, which are incorporated in and constitute part of the specification, illustrate a presently preferred embodiment of the invention and together with the general description given above and detailed description of the preferred embodiment given below, serve to explain the principles of the invention.

FIG. 10 illustrates a side view of a fifth embodiment of a fiducial marker-sensor device of the present invention;

FIG. 11 illustrates a side view of a fiducial marker according to the fifth embodiment of the fiducial marker-sensor device of the present invention;

FIG. 12 illustrates a side view of sensor ring according to the fifth embodiment of the fiducial marker-sensor device of the present invention;

FIG. 13 illustrates a schematic view of a sixth embodiment of a fiducial marker-sensor device of the present invention;

FIG. 14 illustrates a schematic view of a seventh embodiment of a fiducial marker-sensor device of the present invention;

FIG. 15 illustrates a medical instrument for use in the registration system of the present invention.

DETAILED DESCRIPTION OF DRAWINGS

Reference will now be made in detail to the present preferred exemplary embodiments of the invention, examples of which are illustrated in the accompanying drawings. Wherever possible, the same reference numbers will be used throughout the drawings to refer to the same or like parts.

In accordance with the present invention, a method for use during a procedure on a body generates a display representing relative positions of two structures during the procedure. The method comprises the steps of (i) storing an image data set in memory, the image data set representing the position of the body based on scans taken of the body prior to the procedure;

(ii) reading the image data set stored in the memory, the image data set having a plurality of data points in known relation to a plurality of reference points for at least one of the two structures; (iii) placing one or more magnetic field sensors in known relation to the reference points of the two structures; (iv) generating a magnetic field; (v) detecting the magnetic field with the magnetic field sensors; (vi) ascertaining the locations of the sensors based upon the magnetic field detected by the sensors and processing the locations of the sensors to generate a displaced image data set representing the relative position of the two structures during the procedure; and (vii) generating a display based on the displaced image data set illustrating the relative position of the two structures during the procedure. The relation of the plurality of data points to the plurality of reference points is determined by the user or by standard image processing of shape detection.

The two structures can be body elements (e.g., vertebrae of the spine) or a body element (e.g., a brain or a vertebrae) and a medical instrument such as a probe.

Figure 1:
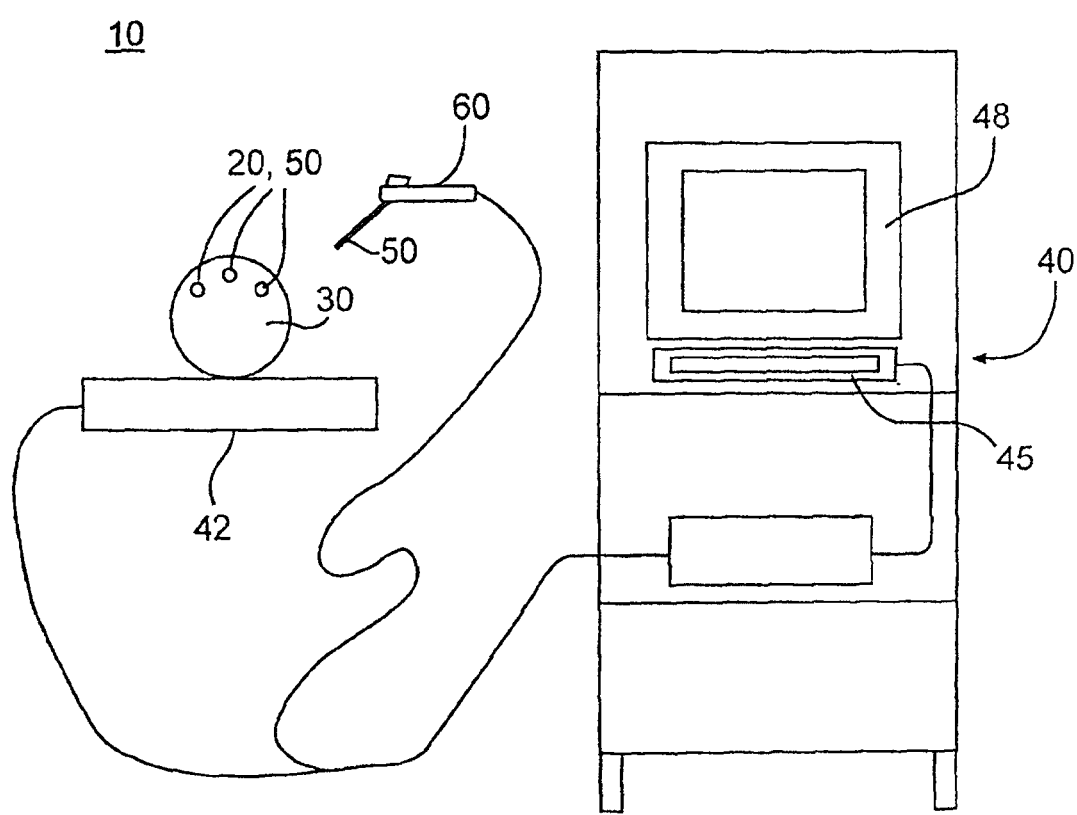
FIG. 1 is a schematic diagram illustrating an embodiment of the registration system of the present invention.

FIG. 1 schematically illustrates an exemplary embodiment of the registration system 10 of the present invention. For illustrative purposes, the registration system of the present invention will be described for a brain surgery procedure. However, the registration system may alternatively be used for a number of different procedures on the body, including spinal surgery (described hereinafter).

Initially, at least one fiducial marker 20 is placed on patient's head 30. A pre-operative scan is taken of the patient's head 30, preferably using at least one of MR, CT, ultrasound, fluoro and PET. The scan generates an image data set that is placed into the memory of a computer system 40. The image data set represents the position of the patient's head 30 based on the pre-operative scans of the head. The image data set includes a plurality of data points.

During the procedure, at least one magnetic field sensor 50 is placed in known relation to the at least one fiducial marker 20 on the patient's head 30. For example, the magnetic field sensor can be integrated with the fiducial marker, attached to the fiducial marker, or interchanged with the fiducial marker. Another magnetic field sensor 50 can be placed, for example, in a medical instrument 60. The medical instrument 60 does not need a fiducial marker because it is not present in the scan taken to create the image data set.

During the procedure, a magnetic field generator (not shown) generates a magnetic field in the area of the patient. For example, coils (not shown) can be embedded into an operating table 42 on which the patient is placed. The magnetic field sensors 50 on the patient's head 30 and in the medical instrument 60 detect the generated magnetic field and send appropriate signals to the processor 45 so that the processor 45 can determine the positions of the magnetic field sensors 50 during the procedure. Once the processor 45 determines the positions of the magnetic field sensors 50 on the patient's head 30, the position of the magnetic field sensors 50 on the patient's head is registered to the position of the fiducial markers 20 as represented in the scan.

After the position of the magnetic field sensors 50 has been determined and the sensors on the patient's head 30 are registered, a displaced image data set is created and displayed on a monitor 48. The display includes the relative position of the medical device 60 to the patient's head 30.

Figure 2:
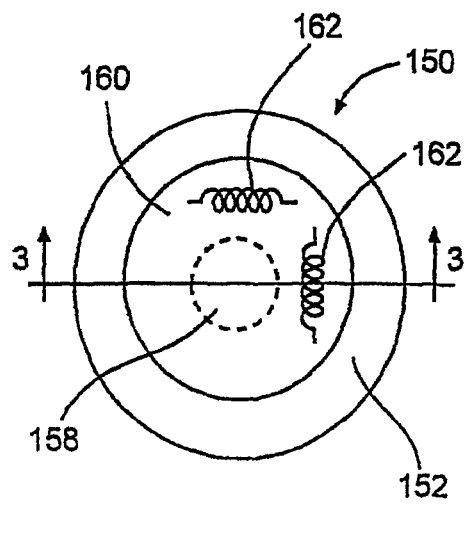
FIG. 2 illustrates a top view of a first embodiment of a fiducial marker-sensor device.
Figure 3:
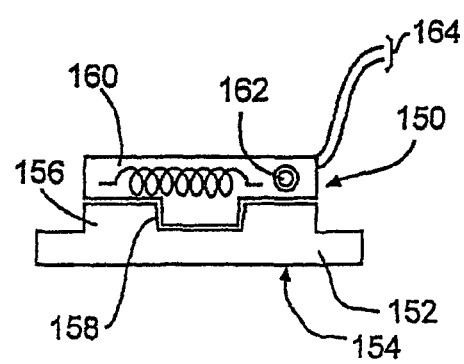
FIG. 3 illustrates a cross-sectional view of the first embodiment of the fiducial marker-sensor device of the present invention, taken along line 3-3 of FIG. 2.

A variety of fiducial markers 20 and magnetic field sensors 50 (combined to create "fiducial marker-sensor devices") are illustrated in FIGS. 2 through 14. In FIGS. 2 and 3, an interchangeable fiducial marker-sensor device 150 is illustrated. The device 150 includes a base 152 that is attached to the patient. The base 152 is preferably adhesively attached to the patient along its bottom surface 154, but may also be implanted in the patient, clamped or stapled to the patient, or otherwise suitably attached to the patient. The base 152 has a raised ring portion 156 and a central circular depression 158. A fiducial (not shown) having a shape complementary to the base 152 is placed into the base for scanning, and then a sensor 160 having a shape complementary to the base 152 is placed in the base for electromagnetic tracking of the patient space. One or more coils 162 are placed in the sensor 160, preferably perpendicular to each other. The coils 162 are placed in communication with the processor 45, for example using wires 164 or similarly suitable communication links such as radio waves. Alternatively, optical, acoustic or inertial elements could be interchanged for the sensor if an optical, acoustic or inertial navigation system is employed.

Figure 4:
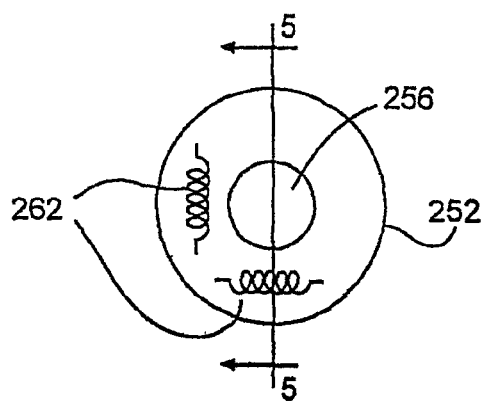
FIG. 4 illustrates a top view of a second embodiment of a fiducial marker-sensor device.
Figure 5:
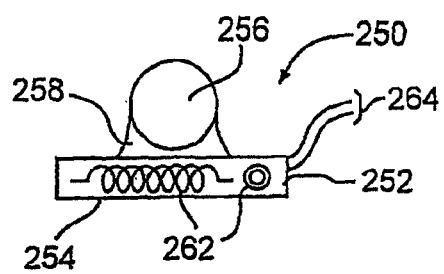
FIG. 5 illustrates a cross-sectional view of the second embodiment of the fiducial marker-sensor device of the present invention, taken along line 5-5 of FIG. 4.

In FIGS. 4 and 5, a preferred embodiment of an integrated fiducial marker-sensor 250 is illustrated. The illustrated fiducial marker 256 is spherical, but provides only location data and no orientation data. The device 250 includes a base 252 that is attached to the patient. The base 252 is preferably adhesively attached to the patient along its bottom surface 254, but may also be implanted in the patient, clamped or stapled to the patient, or otherwise suitably attached to the patient. The fiducial marker 256 is attached to the base 252, for example using an epoxy or plastic layer 258. The base is also a sensor for electromagnetic tracking of the patient space. One or more coils 262 are placed in the base 252, preferably perpendicular to each other. The coils 262 are placed in communication with the processor 45, for example using wires 264 or other suitable communication links such as radio waves. Alternatively, optical, acoustic or inertial elements known in the art could be interchanged for the sensor if an optical, acoustic or inertial navigation system is employed.

The preferred size of the spherical fiducial marker is dependent upon scan slice thickness. For example, with 1 mm slices, a 3 mm sphere is preferred and for 3 mm slices an 8 mm sphere is preferred. As can be see in FIGS. 3 and 4, the spherical fiducial marker 256 is spaced from the base. It is preferable (but not necessary) that the space between the fiducial marker and the patient is greater than the slice thickness to provide a "barrier." By barrier, the present invention contemplates that the fiducial is preferably spaced from the patient's skin by a large enough distance that the fiducial and the skin do not blend together in the scan image and appear as one object.

Figure 6:
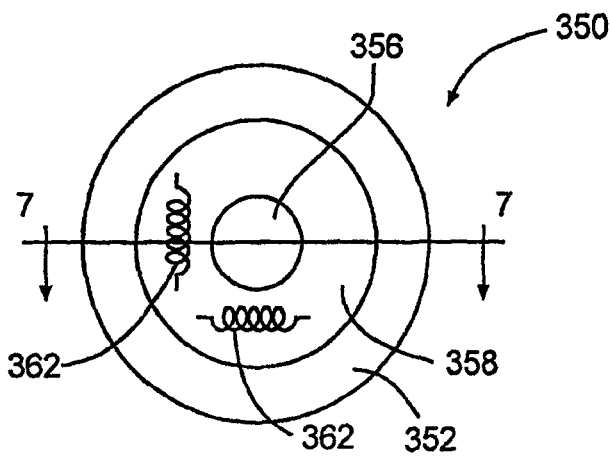
FIG. 6 illustrates a top view of a third embodiment of a fiducial marker-sensor device.
Figure 7:
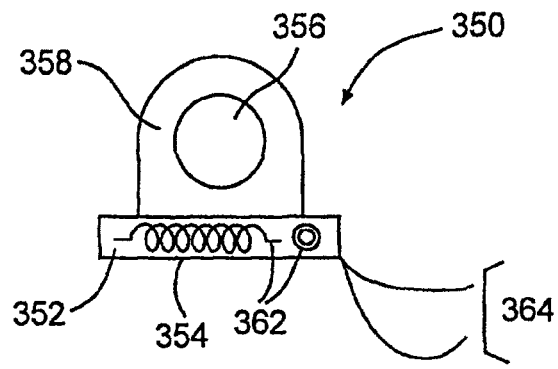
FIG. 7 illustrates a cross-sectional view of the third embodiment of the fiducial marker-sensor device of the present invention, taken along line 7-7 of the FIG. 6.

In FIGS. 6 and 7, another preferred embodiment of an integrated fiducial marker-sensor 350 is illustrated. The illustrated fiducial marker 356 has a spherical shape. The device 350 includes a base 352 that is attached to the patient either adhesively along its bottom surface 354, implanted in the patient, clamped or stapled to the patient, or otherwise suitably attached to the patient. The fiducial marker 356 is attached to the base 352, for example using an epoxy or plastic casing 358. The base is also a sensor for electromagnetic tracking of the patient space. One or more coils 362 are placed in the base 352, preferably perpendicular to each other. The coils 362 are placed in communication with the processor 45, for example using wires 364. Alternatively, optical, acoustic or inertial elements could be interchanged for the sensor if an optical, acoustic or inertial navigation system is employed.

As stated above, the preferred size of the spherical fiducial marker is dependent upon scan slice thickness, and the spherical fiducial marker 356 is preferably (but not necessarily) spaced from the base a distance greater than the slice thickness to provide a barrier.

Figure 8:
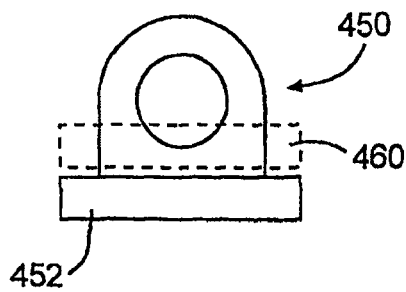
FIG. 8 illustrates a side view of a fourth embodiment of a fiducial marker-sensor device of the present invention, indicating a placement of an attachable sensor ring in phantom.
Figure 9:
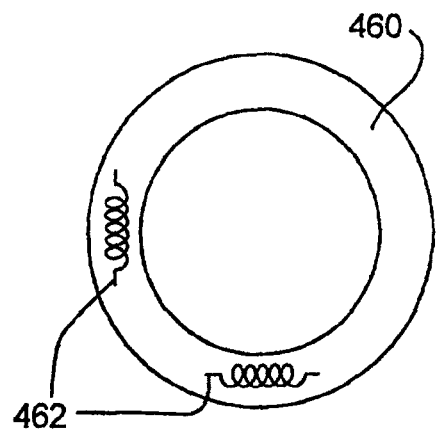
FIG. 9 illustrates a top view of an attachable sensor ring for placement according to the fourth embodiment of the fiducial-sensor device as illustrated in FIG. 4.

FIGS. 8 and 9 illustrate a fiducial marker-sensor device 450 similar to the fiducial marker-sensor device illustrated in FIGS. 6 and 7, except that the sensor is in an attachable ring 460 instead of being in the base 452. This embodiment allows attachment of the sensor in known relation to the fiducial after scanning has taken place. As with the above-described embodiments, the sensor includes at least one sensor 462, and preferably includes two perpendicularly oriented sensors 462.

FIGS. 10 through 12 illustrate an interchangeable fiducial marker-sensor device 550 including a base 552 having a protrusion 554 that is threaded. A fiducial marker 570 has a complementary threaded recess 572 for engagement with the protrusion 554 on the base 552. FIG. 11 illustrates the fiducial marker 570. FIG. 12 illustrates a sensor ring 560 with an aperture 562 that is threaded so that it can be interchanged with the fiducial marker 570 on the base 552. Alternatively, this embodiment could also employ a recess in the base and a complementary protrusion on the interchangeable fiducial marker and sensor ring.

The present invention contemplates use of a fiducial marker having a unique geometrical shape in any of the embodiments of the fiducial marker-sensor device described hereinabove. In addition, the present invention contemplates placement of multiple fiducial markers on the patient and attachment of sensors to a subset of the fiducial markers that the user finds are most clearly and helpfully represented in the scan. Placement of additional sensors helps ensure that a proper number of sensors can be placed on the patient even if one or more fiducial markers are not clearly identifiable in the scan.

One exemplary embodiment of the method of the present invention utilizes at least one fiducial marker-sensor device. The user places at least one fiducial marker with a unique geometric shape on the patient's head 30. One example of the unique geometrical shape contemplated by the present invention includes at least three distinct non-collinear points, and may include more points to increase the accuracy of the system in correlating patient space to image space. Examples of presently preferred unique geometric shapes including more than three non-collinear points are illustrated in FIGS. 13 and 14. Unique geometrical shapes allows determination of both the location and the orientation of the fiducial marker from the image slices and with a six degree of freedom (DOF) sensor. The image slices represent the location and orientation of the at least one fiducial marker in image space and the six DOF sensor determines the corresponding location and orientation of the at least one fiducial marker in patient space to accomplish auto-registration. The six DOF sensor is preferably electromagnetic, but may also be acoustic, optical or inertial. Other uniquely identifiable shapes can be used, for example a T-shape or a tack.

Alternatively, the user may place at least two fiducial markers with predetermined geometrical shapes (see FIGS. 13 and 14) on the patient's head 30. The location and orientation of the fiducial markers can be determined from the image slices and with a five DOF sensor. A six DOF sensor is not needed, but can be used, when at least two fiducial markers with unique geometries are used. The image slices represent the location and orientation of the fiducial markers in image space and the five DOF sensor determines the corresponding location and orientation of the fiducial markers in patient space to accomplish auto-registration. The five DOF sensor is preferably electromagnetic, but may also be acoustic, optical or inertial.

As another alternative, the user may place at least three fiducial markers on the patient's head 30. The location of the fiducial markers can be determined from the image slices and with a combination of sensors to define six DOF (e.g., two five DOF sensors). The image slices represent at least the location of the fiducial markers in image space and the sensor determines at least the corresponding location of the fiducial markers in patient space to accomplish auto-registration. The sensors are preferably electromagnetic.

In yet another alternative, the user may place at least three fiducial markers on the patient's head 30. In this embodiment including at least three fiducial markers, the fiducial markers need not have a unique geometrical shape. Exemplary embodiments of fiducial markers that do not have a unique geometrical shape are illustrated in FIGS. 4 through 9. The exemplary fiducial marker-sensor devices illustrated in FIGS. 4 through 9 include a spherical fiducial marker. The location of the fiducial markers can be determined from the image slices and with a three DOF sensor. A three DOF sensor is commonly used in both acoustic, optical or inertial navigation systems. The image slices represent the location of the fiducial markers in image space and the three dimensional sensor determines the corresponding location of the fiducial markers in patient space to accomplish auto-registration.

As stated above, once fiducial markers 20 have been placed on the patient's head, image slices or a three-dimensional scan (e.g., MR, CT, ultrasound, fluoro and PET) are taken of the patient's head to create a three-dimensional data set having data points corresponding to reference points on the fiducial marker(s) 20. The relation of the plurality of data points to the plurality of reference points is determined by the user or by standard image processing of shape detection. The scan is preferably taken prior to or during the procedure. An image data set is created by the scan and placed in computer memory, and the processor 45 identifies the fiducial marker(s) in image space (in the image data set) using image algorithms. Each fiducial marker is represented by at least one data point in the image data set.

Preferably, the image data set is created prior to placing the patient on the operating table. Once the patient is ready for surgery, the processor 45 can identify the fiducial marker(s) 20 in patient space using signals received from the sensors 50 on the patient's head 30. Each fiducial marker includes least one reference point 70 in patient space (see exemplary fiducial markers illustrated in FIGS. 13 and 14). The reference points need not be attached to a defined triangle as illustrated in FIG. 13, but instead may be as simple as 3 suspended BBs. The reference points in patient space correlate to the data points in the image data set. The signals sent by the sensors to the processor 45 to identify the fiducial marker(s) in patient space are called "localization information" and allow the processor to "auto-register" the patient by correlating the reference points to the data points. The relation of the plurality of data points to the plurality of reference points is determined by the user or by standard image processing of shape detection. This is done by determining a translation matrix between image space and patient space.

Auto-registering the patient provides a simplified and more user-friendly system because the user need not select the data points in the data set and thereafter touch fiducial markers, or create a surface in patient space by selecting multiple points or scanning and then accept or reject the best fit in image space as determined by the processor, or repeatedly remove and replace a localizing device. In addition, accuracy can be enhanced because opportunities for human error during user registration is eliminated.

During the procedure, at least one sensor 50 is placed in known relation to the fiducial marker(s) 20 on patient's head to create a dynamic reference frame for the procedure. Preferably, the at least one sensor is integrated with the fiducial marker(s), removably attached to the fiducial marker(s), permanently affixed to the fiducial marker(s) after the patient is scanned, or interchanged with the fiducial marker(s) during the procedure. In a preferred embodiment of the invention in which a single uniquely shaped fiducial marker with ascertainable location and orientation is utilized (see FIGS. 13 and 14), the location and orientation of the sensor with respect to the fiducial marker is determined prior to placement of the fiducial marker-sensor onto the patient and remains constant throughout the procedure. For example, factory calibration may be used.

During the procedure, the computer system dynamically tracks movement of the sensors 50 on the patient's head 30 and on the medical instrument 60. Thus, the system tracks movement of the medical instrument 60 relative to the patient's head 30. In addition, the system can "learn the geometry" of sensors placed on the patient's head to perform geometry checks that help maintain system accuracy. To learn the geometry of the sensors 50 on the patient's head, the processor 45 determines the relative locations of all of the sensors 50 on the patient's head. The relative locations of the sensors on the patient's head should not change. If the processor determines that the relative location of sensors on the patient's head has changed, the system indicates to the user that an error may have occurred. By using the magnetic field sensors as a dynamic reference frame, the system need not employ additional navigational devices in the surgical field.

As the system tracks relative movement of two structures such as the patient's head and the medical instrument, a graphical representation of instrument navigation through the patient's brain is displayed on a monitor 48 of the computer system 40 based on reconstructed images of scanned image data.

An exemplary embodiment of a medical instrument for use in the present invention is illustrated in FIG. 15. The medical instrument 60 includes a handle 62 and a probe 64 having a tip portion 66. The tip portion 66 of the medical instrument 60 includes a sensor having at least one coil 68 that makes up the sensor 50. In a preferred embodiment of the invention, the two coils 68 are placed in the tip portion 66 in order to allow the computer system of the present invention to track movement of the instrument in six degrees of freedom. The coils 68 are preferably located perpendicular to each other within the tip portion 66.

When using the registration system of the present invention during spinal surgery, the systems ability to track relative movement of multiple structures is particularly important for at least the following reason. Prior to spinal surgery, the vertebra are scanned to determine their alignment and positioning. During imaging, scans are taken at intervals through the vertebra to create a three-dimensional pre-procedural data set for the vertebra. However, after scanning the patient must be moved to the operating table, causing repositioning of the vertebra. In addition, the respective positions of the vertebra may shift once the patient has been immobilized on the operating table because, unlike the brain, the spine is not held relatively still by a skull-like enveloping structure. Even normal patient respiration may cause relative movement of the vertebra.

Figure 16:
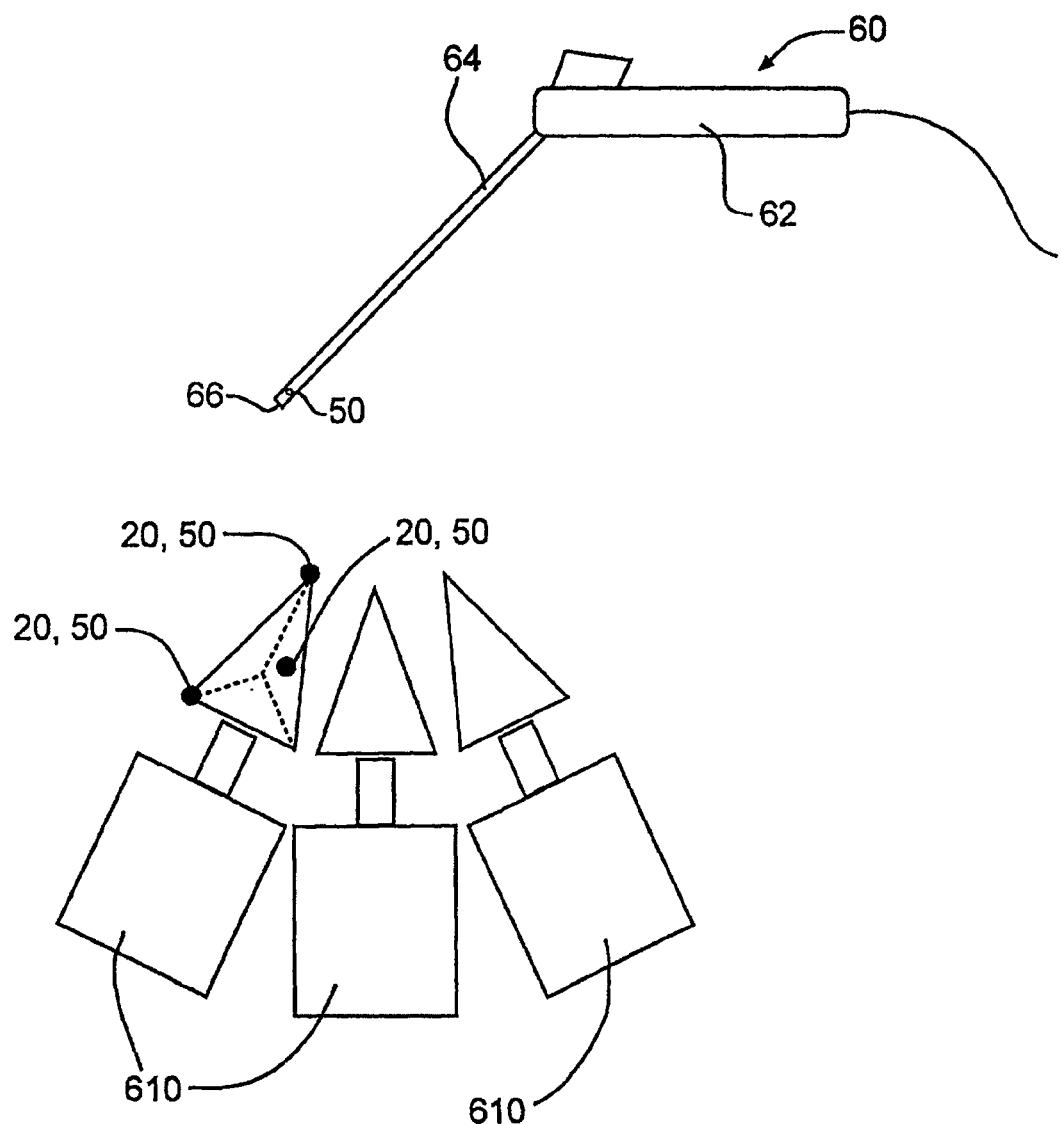
FIG. 16 schematically illustrates the registration system for use in spinal procedures.

FIG. 16 schematically illustrates elements of spinal surgery needed to explain the procedures of the present invention. At least one fiducial marker 20 is placed on each vertebra 610 of concern during the procedure. A vertebra "of concern" is a vertebra whose position the user is concerned with during the spinal procedure. Once at least one fiducial marker 20 has been placed on each vertebra of concern, image slices or a three-dimensional scan (e.g., MR, CT, ultrasound, fluoro and PET) are taken of the patient's spine to create a three-dimensional data set having data points corresponding to reference points on each fiducial marker 20. The relation of the plurality of data points to the plurality of reference points is determined by the user or by standard image processing of shape detection. The scan is preferably taken prior to or during the procedure. An image data set is created by the scan and placed in computer memory, and the processor 45 (see FIG. 1) identifies each fiducial marker 20 in image space (in the image data set) using image algorithms. Each fiducial marker 20 is represented by at least one data point in the image data set.

Preferably, the image data set is created prior to placing the patient on the operating table. Once the patient is ready for surgery, the processor 45 can identify the fiducial marker 20 in patient space using signals received from at least one sensor 50, placed in known relation to the fiducial marker(s) 20 placed on the patient's vertebra 610. As described above, the system then auto-registers the patient by correlating the reference points to the data points. According to the present invention, the fiducial marker-sensor devices illustrated with respect to brain surgery are equally acceptable for spinal surgery.

During the procedure, the computer system dynamically tracks movement of each sensor 50 on the patient's vertebra and on the medical instrument 60. Thus, the system tracks alignment and positioning of the vertebra 610 (e.g., relative movement of the vertebra) as well as movement of the medical instrument 60 relative to the vertebrae. In addition, the system can "learn the geometry" of sensors placed on a single to perform geometry checks that help maintain system accuracy as described above.

As the system tracks relative movement of vertebra 610 and the medical instrument 60, a graphical representation of instrument navigation through the patient's spinous process is displayed on a monitor 48 of the computer system 40 based on reconstructed images of scanned image data.

An exemplary embodiment of a medical instrument for use in the present invention is illustrated in FIG. 15. The medical instrument 60 includes a handle 62 and a probe 64 having a tip portion 66. The tip portion 66 of the medical instrument 60 includes a sensor having at least one coil 68. In a preferred embodiment of the invention, the two coils 68 are placed in the tip portion 66 in order to allow the computer system of the present invention to track movement of the instrument in six degrees of freedom. The coils 68 are preferably located perpendicular to each other within the tip portion 66.

It will be apparent to those skilled in the art that various modifications and variations can be made in the registration system of the present invention and in construction of this registration system without departing from the scope or spirit of the invention. As an example a variety of other embodiments of the fiducial marker-sensor device could be employed, including fiducial markers of an endless variety of shapes and sizes. The magnetic field generator and sensor roles could be reversed, such that the operating table 42 could include a sensor, and field generators could be placed on the patient and in the medical device. In addition, an optical, acoustic or inertial system could be used to track the location of the sensors and fiducial markers instead of electromagnetics.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for displaying relative positions of two structures during a procedure on a body, the system comprising:
    a memory for storing an image data set representing the position of the body based on scans of the body, the image data set having a plurality of data points in known relation to a plurality of reference points for the body;
    a magnetic field generator for generating a magnetic field;
    a plurality of magnetic field sensors placed in known relation to at least one of the plurality of reference points for the body, the plurality of magnetic field sensors operable to sense the magnetic field and to generate a position signal in response to the sensed magnetic field;
    a processor configured to execute instructions to,
        receive the position signal for ascertaining a location of at least a first sub-plurality of the plurality of magnetic field sensors based upon the position signal,
        register the ascertained location of at least the first sub-plurality of the plurality of magnetic field sensors and the image data set based on the known relation of at least the first sub-plurality of the plurality of magnetic field sensors relative to the at least one of the plurality of reference points and the received position signal from at least the first sub-plurality of the plurality of magnetic field sensors,
        generate a displaced image data set representing relative positions of the plurality of reference points for the body during the procedure based on the registered image data set; and
        learn a geometry of relative locations of at least a second sub-plurality of the plurality of magnetic field sensors placed on the body at a first time to perform an accuracy geometry check at a second time to ensure accuracy after the registration, wherein the second sub-plurality of the plurality of magnetic field sensors placed on the body are configured to remain substantially fixed in the learned geometry between the first time and the second time; and
    a display to display the displaced image data set generated by the processor to display the relative position of the plurality of reference points for the body during the procedure.

2. The system of claim 1, wherein the plurality of reference points are identifiable as points on body elements of the body to which the image data set relates.

3. The system of claim 1, further comprising:
    a fiducial marker, wherein the fiducial marker defines the plurality of reference points for the body in the image data set;
    wherein the fiducial marker is placed on the body prior to the image data set being acquired of the body;
    wherein the processor is further configured to identify the fiducial marker in the image data set using image algorithms and wherein the fiducial marker is represented by at least the plurality of reference points in the image data set.

4. The system of claim 3, wherein the image data set is a three-dimensional data set that has data points corresponding to the plurality of reference points defined by the fiducial marker.

5. The system of claim 4,
    wherein the first sub-plurality of the plurality of magnetic field sensors is placed on a first vertebra on the body and at least the second sub-plurality of the plurality of magnetic field sensors is placed on a second vertebra on the body;
    wherein the processor is configured to dynamically track movement of each of the first sub-plurality of magnetic field sensors and the second sub-plurality of magnetic field sensors to track alignment and positioning of both the first vertebra and the second vertebra.

6. The system of claim 5, wherein the processor is configured to track relative movement of both the first vertebra and the second vertebra.

7. The system of claim 1, further comprising:
    an instrument operable to be moved relative to the body; and
    an instrument magnetic field sensor configured to sense the magnetic field and to generate an instrument position signal in response to the sensed magnetic field;
    wherein the processor is configured to determine the relative location of the instrument relative to the body based on the instrument position signal and the position signal and generate for display with the display a representation of the instrument relative to the body.

8. A system for displaying relative positions of two structures during a procedure on a body, the system comprising:
    a first fiducial marker that defines at least a first reference point and a second fiducial marker that defines at least a second reference point, both operable to be connected to the body during an acquisition of an image data set representing the body;
    a memory for storing the image data set representing the body, the image data set having a plurality of body data points in known relation to the first reference point and the second reference point;
    a magnetic field generator for generating a magnetic field;
    a first magnetic field sensor placed in known relation to the first reference point on a first body portion of the body and a second magnetic field sensor placed in known relation to the second reference point on a second body portion of the body, the first magnetic field sensor operable to sense the magnetic field and to generate a first position signal in response to the sensed magnetic field and the second magnetic field sensor operable to sense the magnetic field and to generate a second position signal in response to the sensed magnetic field;
    a processor Configured to,
        receive the first position signal and the second position signal,
        ascertain a location of both the first Magnetic field sensor and the second magnetic field sensor based upon the received first position signal and the second position signal,
        register the first magnetic field sensor and the second magnetic field sensor and the image data set based on both the known relation of the first magnetic field sensor relative to the first reference point and the ascertained location of the first magnetic field sensor and the known relation of the second magnetic field sensor relative to the second reference point and the ascertained location of the second magnetic field sensor, and generate a displaced image data set representing relative positions of the first reference point and the second reference point for the body during the procedure based on the registered image data set;

determine a fixed geometry between the first magnetic field sensor and the second magnetic field sensor, wherein the first magnetic field sensor is positioned at the fixed geometry relative to the second magnetic field sensor; and increase accuracy of the registered image data set by performing an accuracy check based on the determined fixed geometry and tracking the determined fixed geometry during the procedure; and a display to display the displaced image data set generated by the processor to display the relative position of the first reference point and the second reference point for the body during the procedure.

9. The system of claim 8, wherein the first fiducial marker and the first magnetic field sensor are integrated into a single unit.

10. The system of claim 9, wherein the first reference point defined by the first fiducial marker is positioned a distance away from a connection portion of the first fiducial marker relative to the body.

11. The system of claim 8, wherein the first fiducial marker and the first magnetic field sensor are configured to be connected;

wherein the image data set is configured to be acquired with the first fiducial marker connected to the first body portion and the first magnetic field sensor is configured to be connected after the acquisition of the image data set.

12. The system of claim 11, wherein the processor is configured to register the image data set automatically based on the known relation of the first magnetic sensor relative to the first fiducial marker.

13. The system of claim 11, wherein the first reference point defined by the first fiducial marker is positioned a distance away from a connection portion of the first fiducial marker relative to the body.

14. A method for displaying relative positions of two structures during a procedure on a body, the method comprising:

accessing an image data set representing the position of the body based on scans of the body, the image data set having a plurality of data points in known relation to a plurality of reference points for the body;

generating a magnetic field with a magnetic field generator;

generating a first position signal with a first magnetic field sensor placed in known relation to at least one of the plurality of reference points for the body on a first body portion, wherein the first position signal from the first magnetic field sensor is in response to the sensed magnetic field;

generating a second position signal with a second magnetic field sensor placed in known relation to at least one of the plurality of reference points for the body on a second body portion, wherein the second position signal from the second magnetic field sensor is in response to the sensed magnetic field;

receiving the first position signal and the second position signal with a processor to ascertain a location of both the first magnetic field sensor and the second magnetic field sensor based upon the received first position signal and the second position signal;

registering, with the processor configured to register, the first magnetic field sensor and the second magnetic field sensor and the image data set based on the known relation of the first magnetic field sensor relative to the at least one of the plurality of reference points for the body on a first body portion and the second magnetic field sensor relative to the at least one of the plurality of reference points on the second body portion and the ascertained location of both the first magnetic field sensor and the second magnetic field sensor based upon the received first position signal and the received second position signal;

generating a displaced image data set with the processor representing relative positions of the plurality of reference points for the body during the procedure based on the registered image data set;

displaying the displaced image data set generated by the processor to display the relative position of the plurality of reference points for the body during the procedure;

determining a fixed geometry between the first magnetic field sensor and the second magnetic field sensor, wherein the first magnetic field sensor is positioned at the fixed geometry relative to the second magnetic field sensor; and performing an accuracy check with the determined fixed geometry and tracking the geometry during the procedure to increase accuracy of the registered image data set.

15. The method of claim 14, wherein the first magnetic field sensor is connected to a first vertebra and the second magnetic field sensor is attached to a second vertebra separate from the first vertebra.

16. The method of claim 15, further comprising:

sensing the magnetic field with an instrument magnetic field sensor affixed to an instrument;

generating an instrument position signal in response to the sensed magnetic field with the instrument magnetic field sensor;

determining the relative location of the instrument relative to the body with the processor based on the instrument position signal and the ascertained location of both the first magnetic field sensor and the second magnetic field sensor based upon the received first position signal and the second position signal and generate for display with the display a representation of the instrument relative to the body.

17. The method of claim 16, wherein the instrument magnetic field sensor includes a first coil and a second coil positioned near a tip portion of the instrument.

18. The method of claim 17, wherein the first coil is positioned substantially orthogonal to the second coil to ascertain six degree of freedom of movement information regarding the instrument.

19. The method of claim 18, further comprising:

identifying a fiducial marker in image data set using image algorithms and wherein the fiducial marker is represented by at least the plurality of reference points in the image data set.

20. The method of claim 19, wherein identifying the fiducial marker includes at least a first fiducial marker and a second fiducial marker;

wherein the first magnetic field sensor is positioned on the first vertebra relative to the first fiducial Marker and the second magnetic field sensor is positioned on the second vertebra relative to the second fiducial marker;

wherein registering is automatically registering the image data with the processor based upon the known relative location of both the first magnetic field sensor relative to the first fiducial marker and the second magnetic field sensor relative to the second fiducial marker.

* * * * *